United States Patent [19]
Pohlke et al.

[11] 3,993,760
[45] *Nov. 23, 1976

[54] PYRAZINOISOQUINOLINES AS ANTHELMINTIC AGENTS

[75] Inventors: Rolf Pohlke; Friedrich Loebich; Jurgen Seubert, all of Darmstadt; Herbert Thomas; Peter Andrews, both of Wuppertal-Elberfeld, all of Germany

[73] Assignee: Merck Patent Gesellschaft mit beschrankter Haftung, Darmstadt, Germany

[ * ] Notice: The portion of the term of this patent subsequent to Nov. 23, 1993, has been disclaimed.

[22] Filed: June 21, 1974

[21] Appl. No.: 481,792

[30] Foreign Application Priority Data
June 22, 1973 Germany............................ 2331713

[52] U.S. Cl. ............................................. 424/250
[51] Int. Cl.² ..................................... A61K 31/495
[58] Field of Search ..................................... 424/250

[56] References Cited
FOREIGN PATENTS OR APPLICATIONS
1,470,062   5/1969   Germany ........................... 424/250

Primary Examiner—Jerome D. Goldberg
Attorney, Agent, or Firm—Millen, Raptes &. White

[57] ABSTRACT

(−)-2-Benzoyl-4-oxo-1,2,3,6,7,11b-hexahydro-4H-pyrazino[2,1-a]isoquinoline is prepared by benzoylation of (−)-4-oxo-1,2,3,6,7,11b-hexahydro-4H-pyrazino[2,1-a]isoquinoline, or cyclization of a compound of the formula

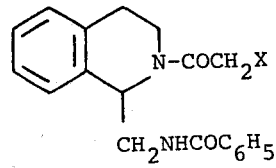

wherein X is F, Cl, Br, I or O-tosyl and which has the optical configuration of the final product, or cyclization of a compound of the formula

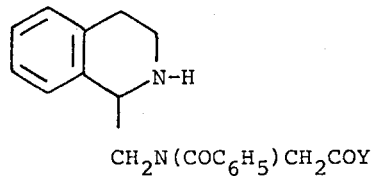

wherein Y is OH, alkoxy, F, Cl, Br or I under HY-removing reaction conditions and which has the optical configuration of the final product, which is an anthelmintic.

10 Claims, No Drawings

PYRAZINOISOQUINOLINES AS ANTHELMINTIC AGENTS

BACKGROUND OF THE INVENTION

This invention relates to the isolated laevorotatory isomer of 2-benzoyl-4-oxo-1,2,3,6,7,11b-hexahydro-4H-pyrazino[2,1-a]isoquinoline (Compound A), which exhibits excellent and unexpectedly high anthelmintic activity.

In the literature and in practice, several compounds are known which are effective against one or more tapeworm (cestode) types, for example, niclosamide [N-(2-chloro-4-nitrophenyl)-5-chlorosalicylamide], quinacrine [2-methoxy-6-chloro-9-[(1-methyl-4-diethylaminobutyl)-amino]-acridine], dichlorophene(2-,2'-dihydroxy-5,5'-dichlorodiphenylmethane).

These agents, however, are in part ineffective against the larval forms of the cestodes, as well as against those adult tapeworms which are not located in the intestinal lumen. Also, the echinococci, e.g., Echinococcus granulosus, have been difficult to combat heretofore and the results have not always been completely satisfactory. Additionally, with several of these agents, e.g., quinacrine and dichlorophene, considerable undesired side effects, e.g., vomiting, nausea, can be expected.

It is possible to utilize other compounds for the combatting of schistosomes, for example antimony-containing agents, e.g., stibophen [sodium antimony bis(-pyrocatechol-2,4-disulfonate)], niridazole [1-(5-nitro-2-thiazolyl)-imidazolidin-2-one], lucanthone [1-(2-diethylaminoethylamino)-4-methylthiaxanthone hydrochloride], etc. However, all these known compounds are not optimally effective against the various forms of schistosomiasis, so that they can be utilized without problems, e.g., mass treatment of whole populations.

The anthelmintic properties of Compound A exceed to a surprisingly degree those of the racemic 2-benzoyl-4-oxo-1,2,3,6,7,11b-hexahydro-4H-pyrazino[2,1-a]isoquinoline (Compound B), which is the subject of Application Ser. No. 449,690, filed Mar. 11, 1974.

SUMMARY OF THE INVENTION

In one composition aspect, this invention relates to the laevorotatory isomer of 2-benzoyl-4-oxo-1,2,3,6,7,11b-hexahydro-4H-pyrazino[2,1-a]isoquinoline (Compound A), substantially free from its dextrorotatory optical isomer.

In another composition aspect, this invention relates to anthelmintic compositions comprising an anthelmintically effective unit dosage amount of Compound A in admixture with a pharmaceutically acceptable carrier, viz., at least one solid, liquid or semiliquid vehicle or additive, and optionally, at least one further anthelmintically effective agent.

In its method of use aspect, this invention relates to the treatment of cestodial, trematodial infestations with a composition of this invention.

DETAILED DISCUSSION

The laevorotatory isomer of 2-benzoyl-4-oxo-1,2,3,6,7,11b-hexahydro-4H-pyrazino[2,1-a]isoquinoline (Compound A) exhibits excellent and unexpected high activity as an anthelmintic. The term "anthelmintic" as used herein means a composition which is effective against parasitic worms, including those existing within and also outside of the gastrointestinal tract of humans and animals.

Compound A exhibits its anthelmintic activity on hymenolysis nana in a dose which is up to five times smaller than that of the racemic 2-benzoyl-4-oxo-1,2,3,6,7,11b-hexahydro-4H-pyrazino[2,1-a]isoquinoline (Compound B). This effect could not be expected, since one would anticipate a doubling of the efficiency at most, if only one isomer were active.

The effectiveness of Compound A extends to larval and adult cestodes of a great variety of genera, e.g., Taenia sp., Hymenolepis sp., Raillietina sp., Dipylidium sp., and especially Echinococcus sp. Compound A also has a good effect on trematodes, e.g., of the genus Schistosoma, the species of which cause bilharziosis (Schistosomiasis), a serious tropical disease.

Compound A, as an anthelmintic, has the advantage of being widely applicable as an anthelmintic and having a low toxicity compared to known anthelmintics.

Thus, Compound A is as effective as quinacrine on various types of cestodes, but is less toxic and unlike quinacrine can also be utilized to combat Echinococcus infections, for example, Echinococcus multilocularis, in dogs.

Compound A is also effective against those tapeworms which are difficult to treat therapeutically, for example, Hymenolepis nana in the ileum and Hymenolepis microstoma in the bile duct of mice.

Compound A is effective not only against adult tapeworms, but also against its various larval forms, e.g., against the cysticerci, coenuri, echinococchi, cysticercoids and plerocercoids.

In contrast to niclosamide and other conventional tapeworm medicines, Compound A is effective against schistosomes. In this connection, Compound A has the advantage over schistosonicidal agents such as, for example, stibophen, niridazol, or lucanthone, of being less toxic at its effective dose, so that Compound A can be considered for the treatment of a large number of patients suffering from bilharziosis (mass treatment in infested areas) without having to employ large numbers of medical personnel.

Therefore, Compound A can be utilized as an anthelmintic in humans as well as in veterinary medicine.

Of the two antipodes of 2-benzoyl-4-oxo-1,2,3,6,7,11b-hexahydro-4H-pyrazino[2,1-a]isoquinoline, only the laevorotatory isomer (Compound A) is active as an anthelmintic.

Compound A can be prepared by reacting the laevorotatory isomer of 4-oxo-1,2,3,6,7,11b-hexahydro-4H-pyrazino[2,1-a]isoquinoline with a benzoylating agent, or reacting a compound of Formula I

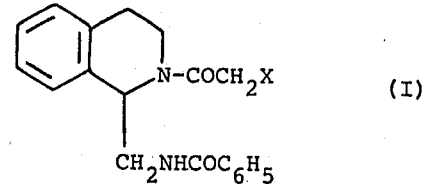

having the same optical configuration as Compound A, wherein X is F, Cl, Br, I or O-tosyl, with a cyclizing agent, or cyclizing a compound of Formula II

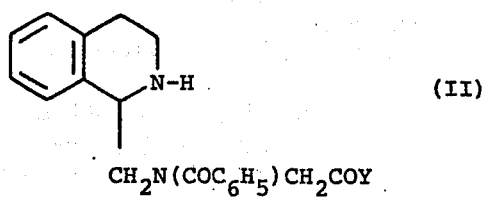

having the same optical configuration as Compound A, wherein Y is OH, alkoxy of 1 to 6 carbon atoms, F, Cl, Br or I under HY-removing reaction conditions.

In Formula II, the alkoxy group can be straight or branched chain, e.g., methoxy, ethoxy, n-propoxy, isopropoxy, and in addition n-butoxy, isobutoxy, sec.-butoxy, tert.-butoxy, n-pentoxy and n-hexoxy.

The benzoylation of (−)-4-oxo-1,2,3,6,7,11b-hexahydro-4H-pyrazino[2,1-a]isoquinoline can be accomplished by methods known from the literature employing any conventional benzoylating agent, e.g., benzoic acid or a functional derivative thereof. The benzoic acid esters, e.g., the methyl-, ethyl-, or isopropylester, benzoic acid anhydride and benzoic acid halogenides, e.g., the chloride, bromide or iodide, are suitable as functional derivatives of benzoic acid. An excess of the benzoic acid derivative can be used as solvent or the reaction can be conducted in the presence of an inert solvent, e.g., benzene, toluene, tetrahydrofuran, dioxan, chloroform or carbon tetrachloride.

A base, e.g., NaOH, KOH, sodium- or potassium carbonate, pyridine, triethylamine and the like, is preferably employed in the benzoylation. The reaction is preferably conducted at about room temperature. The reaction is usually complete in about 10 minutes to 48 hours, usually from 30 minutes to 5 hours.

It is also possible to prepare benzoic acid halogenides in situ from benzoic acid and a halogenating reagent, e.g., an inorganic halogenide or inorganic oxyhalogenide, e.g., silicon tetrachloride, phosphorus trichloride or -tribromide, phosphorus oxychloride or phosphorus pentachloride. Methods known from the literature can be used for this variation of the process also.

The (−)-4-oxo-1,2,3,6,7,11b-hexahydro-4H-pyrazino[2,1-a]isoquinoline used as starting material can be prepared according to several methods. It is possible, e.g., to convert the racemic (±)-2-benzoyl-4-oxo-1,2,3,6,7,11b-hexahydro-4H-pyrazino[2,1-a]isoquinoline to the racemic (±)-4-oxo-1,2,3,6,7,11b-hexahydro-4H-pyrazino[2,1-a]isoquinoline by the action of methanolic hydrochloric acid with subsequently heating, which compound can be resolved into its antipodes according to known methods, e.g., by treatment with an optically active acid. The thus-obtained mixture of diastereomeric salts is then resolved by fractional crystallization or manual selection and liberating the desired optically active base by treating the corresponding separated optically active salt with a strong base. For details related to this method of resolution, see, e.g., Houben-Weyl, Vol. IV, Stuttgart 1955, pages 509–519. It is also possible to use optical active acid ion exchangers for purposes of resolution.

It is also possible to obtain Compound A from a compound of Formula I having the same optical configuration employing a cyclizing agent according to procedures described in the literature. Strong bases are suitable cyclizing agents, especially lithium butyl or potassium tert.-butylate. Others are sodium and potassium methylate, -ethylate, -propylate, -isopropylate, -n-butylate, -tert.-butylate, amides, e.g., lithium diisopropylamide and the corresponding sodium- and potassium amides.

As a rule, the reaction is conducted in an inert solvent, such as benzene, hexane, tert.-butanol, tetrahydrofuran, hexamethyl phosphoric acid triamide, dioxan, ether, dimethylformamide, dimethylsulfoxide or acetonitrile, if desired under nitrogen. Reaction temperatures between 0° C. and the boiling point of the reaction mixture can be employed. The reaction time generally is between 15 minutes and 30 hours, preferably between 10 hours and 14 hours, depending on the temperature employed.

It is also possible to synthesize Compound A analogously to methods known from the literature, e.g., Houben-Weyl, Vol. XI/2, Stuttgart 1958, pages 518–546, by cyclization of a compound of Formula II having the optical configuration corresponding to Compound A under reaction conditions which split off HY.

Usually the reaction is conducted without a solvent with the compound of Formula II being heated to a temperature above its melting point. The reaction can be carried out at normal pressure or under a vacuum. It is also possible to carry out the reaction in the presence of a cyclizing promoting agent, e.g., phosphorus trichloride, phosphorus pentachloride, thionylchloride, phosphorus oxychloride, tetrachlorosilane and dicyclohexylcarbodiimide, in which case it is desirable to use an inert solvent, such as diethylether, dioxane, tetrahydrofuran. This method can be conducted, e.g., at room temperature up to the boiling point of the reaction mixture. The reaction times are usually between 30 minutes and 36 hours, preferably between 1 hour and 5 hours.

A compound of Formula II wherein Y = OH and having an optical configuration corresponding to Compound A, can be cyclized by treatment, e.g., with thionyl chloride in the presence of a base, such as triethylamine, which produces a compound of Formula II wherein Y = Cl, which then cyclizes in situ.

Compound A is active primarily against cestodes and trematodes. It can be used, for example, against the following cestodes, e.g., in the following hosts:

1. *Ruminants:* Moniezia, Stilesia, Avitellina, Thysanienzia, cysticerci of Taenia sp., Coenuris cerebralis, cysticerci of Echinococci. 2. *Equines:* Anoplocephala. 3. *Rodents:* Hymenolepis (especially H. nana and H. diminuta). 4. *Fowl:* Davainea, Raillietina, Hymenolepis. 5. *Canines and Felines:* Taenia (especially T. hydatigena, T. pisiformis, T. taeniaeformis, T. ovis, T. serialis, T. cervi, T. multiceps), Dipylidium (especially D. caninum), Echinococcus (particularly E. granulosus and E. multilocularis). 6. *Humans:* Taenia (especially T. solium, T. saginata, T. serialis, T. multiceps), Hymenolepis (particularly H. nana and H. diminuta), Drepanidotaenia, Dipylidium, Diplopylidium, Coenurus (especially C. cerebralis), Diphyllobothrium (particularly D. latum), Echinococcus cysticerci (especially E. granulosus and E. multilocularis).

Among the trematodes important from the viewpoint of human and veterinary medicine are primarily those of the family of the Schistosoma (Sch. mansoni, Sch. haematobium, Sch. japonicum), infestations of all of which can be treated successfully with Compound A.

Compound A is also useful for the treatment of infestations by, e.g., the genera Fasciola, Dicrocoelium, Clonorchis, Opisthorchis, Paragonimus, Paramphistomum, Fasciolopsis.

Compound A can be administered to numerous host and/or intermediate host organisms for combatting infestations by cestodes or nematodes and/or the larvae thereof. The following species are, inter alia, the main or secondary hosts of tapeworms: humans, the various species of monkeys, as well as the important domestic and wild animals, e.g., the various Canidae, e.g., dog, fox; Felidae, e.g., the cat; Equidae, e.g., the horse, donkey, mule; Cervidae, e.g., the deer, red deer, fallow deer; chamoir; Rodents; Ruminants, e.g., cattle, sheep, goat; birds, e.g., chickens, ducks; pigs and fish.

Infestations by parasites and/or their larvae in the gastrointestinal tract, for example, the stomach, the small intestine, the large intestine, the appendix, the pancreas and the bile duct, can be combatted particularly satisfactorily. However, good effects can also be achieved in various other organs and sites of infection, e.g., liver, kidney, lungs, heart, spleen, lymphatic glands, brain, spinal cord, testes, the abdominal cavity, the subcutaneous, intramuscular and subserous connective tissue, musculature, peritoneum, pleura, diaphragm, blood vessels, e.g., veins, portal vein and arteries.

Compound A is absorbed systemically and thus is also effective against parasitical infestations outside of the gastrointestinal tract, for example, by species of Schistosoma in the vascular system, Hymenolepis microstoma in the bile duct and T. hydatigena cysticerci in the liver.

Compound A can be administered as such or in combination with a wide variety of solid, liquid or semiliquid pharmaceutically acceptable vehicles. Suitable forms of administration are, in combination with various inert vehicles, tablets, dragees, effervescent tablets; tablets or dragees containing the effective agent in depot form; capsules, granules, aqueous suspensions; injection solutions, emulsions, and suspensions; elixirs, syrups, pastes and the like. Such vehicles can comprise solid diluents or fillers, a sterile aqueous medium, as well as various nontoxic organic solvents and the like.

The formulations are produced in the usual manner, for example, by adding Compound A to a solvent and/or excipient, optionally with the use of an emulsifier and/or dispersing agent. When using water as the diluent, nontoxic organic solvents can be utilized as an auxiliary solvent, if desired.

Examples of suitable auxiliary substances for formulating pharmaceutically acceptable carriers are water, nontoxic organic solvents, such as paraffins (e.g., petroleum fractions), vegetable oils (e.g., sesame oil), alcohols (e.g., ethyl alcohol, glycerin), glycols (e.g., propylene glycol, polyethylene glycol); solid carriers, such as, for example, natural rock flours (e.g., kaolins, aluminas, talc, chalk), synthetic rock flours (e.g., highly dispersed silicic acid); sugars (e.g., cane sugar, lactose and dextrose); emulsifiers, such as nonionic and anionic emulsifiers (e.g., polyoxyethylene fatty acid esters, polyoxyethylene fatty alcohol esters, alkyl sulfonates and aryl sulfonates), dispersing agents (e.g., methylcellulose, polyvinylpyrrolidone), and lubricants (e.g., magnesium stearate). For oral administration, tablets and dragees can, of course, also contain sweetening additives, sodium citrate, calcium carbonate and dicalcium phosphate, together with various extra substances, such as starch, preferably potato starch, gelatine and the like. Furthermore, lubricants such as magnesium stearate, sodium lauryl sulfate, and talc can be utilized during the tablet-making process.

When aqueous suspensions and/or elixirs intended for oral administration are desired, Compound A additionally can be mixed with various flavor ameliorating agents or coloring agents.

The pharmaceutically acceptable carrier can also be a comestible, e.g., a component of an animal feed or in admixture with fruit juice, milk, flavored carbonated water or other palatable liquid.

For parenteral administration, a solution of Compound A can be used in admixture with a liquid vehicle adapted for parenteral administration.

The effective agent can be administered in the usual manner. Administration is effected preferably orally, but parenteral, especially subcutaneous, as well as dermal application is likewise possible.

In order to effectively combat the adult forms of the cestodes, it is generally advantageous to administer Compound A once or in divided dosages in daily amounts of about 0.01 to 250, preferably about 0.5 to 100 mg/kg. orally and/or subcutaneously. In order to obtain efficient results when combatting the corresponding tapeworm larvae (cysticerci), larger amounts, e.g., of 2.5 to 250 mg/kg. of effective agent may be necessary.

For the effective combatting of Schistosomes, often larger quantities of Compound A may also be necessary, for example, 2.5 – 250 mg/kg.

Compound A is well tolerated at its therapeutically effective dosages.

In some cases, the aforementioned quantities may have to be varied, namely in dependence on the body weight and/or the type of administration, and also on the basis of the species of parasite and its individual behavior toward the medicine, and/or the type of the drug formulation and the time and/or interval at which the administration is effected. Thus, it is sometimes sufficient to administer less than the above-mentioned minimum amount and in other cases the above-indicated upper limit is sometimes exceeded.

As will be apparent, this invention contemplates both single and successive daily effective doses, the number being dependent upon the severity of infestation and the susceptibility of the particular parasite to Compound A.

Compound A is preferably administered in admixture with a comestible or a pharmaceutically acceptable carrier, viz., the aforementioned vehicles and/or auxiliary agents, but it is in some cases also possible to administer Compound A in the absence or substantial absence of such auxiliary agents, e.g., if Compound A is contained in capsules.

Depending on the manner in which the drug is administered, the ratio between Compound A and the pharmaceutically acceptable carrier, i.e., vehicle or auxiliary agent, employed can vary greatly. If Compound A is, for example, in the form of a tablet or dragee, approximately 0.01 to 2,500 mg. thereof can be combined with about 1 – 10,000 mg. of the pharmaceutically acceptable carrier, i.e., auxiliary agent. If Compound A is formulated as a premix for a medical fodder, approximately 0.1 – 400 g. of Compound A can be admixed to about 1 kg. of vehicle or auxiliary agent. When formulated in an injection liquid, a solution of one liter of liquid can contain about 0.5 – 100 g. of Compound A, depending on the type of solubilizer. Similarly, about 0.5 – 250 g. of Compound A can be dissolved or suspended in one liter of comestible liquid, e.g., juice.

When administering large amounts of Compound A, it is practicable in some cases to distribute several smaller individual doses over the day. For example, one can administer five separate doses of respectively 200 mg. instead of a single dose of 1,000 mg. The same dosage latitude is provided for the application in human or veterinary medicine.

Compound A can be present in the formulations also in mixtures with other conventional effective agents. Since the effectiveness of Compound A extends primarily to cestodes and trematodes, it is advantageous in order to reach a still broader spectrum of activity to administer it in combination, for example, with an agent effective against nematodes (roundworms). Such a suitable agent is, for example, thiabendazole [2-(4-thiazolyl)benzimidazole] or piperazine.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

2.8 ml triethylamine are added to 4.4 g. of (−)-4-oxo-1,2,3,6,7,11b-hexahydro-4H-pyrazino[2,1-a]isoquinoline dissolved in 50 ml chloroform. Then 2.9 g. of benzoylchloride dissolved in 50 ml. chloroform are added dropwise while the solution is stirred. After 2 hours the reaction mixture is extracted with diluted aqueous hydrochloric acid and with water. The organic layer is dried, treated with charcoal and the solvent is evaporated. Compound A is obtained, m.p. = 132° C (crystallized from ethanol/ether), $[\alpha]_D^{20} = -43.5°$.

The starting material may be obtained as follows: 24.3 g. of (±)-4-oxo-1,2,3,6,7,11b-hexahydro-4H-pyrazino[2,1-a]isoquinoline (m.p. = 118°–119° C; obtainable by treating (±)-2-benzoyl-4-oxo-1,2,3,6,7,11b-hexahydro-4H-pyrazino[2,1-a]isoquinoline with methanolic hydrochloric acid and subsequent heating to 180° C at 15 mm Hg) are dissolved in 100 ml methanol and added to a warm solution of 30 g. quinic acid in 500 ml of methanol. The mixture is refluxed for 15 minutes and then cooled to 20° C. The crystals obtained are separated by filtration, the mother-liquor is evaporated to 100 ml and the crystals precipitating now are separated. The quinic acid salt of (−)-4-oxo-1,2,3,6,7,11b-hexahydro-4H-pyrazino[2,1-a]isoquinoline is obtained; m.p. = 196° C. The salt is dissolved in water, the solution is made alkaline and extracted with chloroform. After drying and evaporating the organic solvent the laevorotatory free base is obtained; m.p. = 120° C, $[\alpha]_D^{20} = -306°$ C.

EXAMPLE 2

4.04 g. of (−)-4-oxo-1,2,3,6,7,11b-hexahydro-4H-pyrazino[2,1-a]isoquinoline, 2.6 g. benzoic acid and 2.6 g. silicon tetrachloride are refluxed in 60 ml pyridine for 1 hour. The reaction mixture is poured onto ice, diluted aqueous hydrochloric acid is added and the mixture is extracted with chloroform. Compound A is obtained after drying and evaporating the solvent; m.p. = 132° C.

EXAMPLE 3

1 ml phosphorous trichloride is added dropwise to a solution of 6.1 g. (−)-4-oxo-1,2,3,6,7,11b-hexahydro-4H-pyrazino[2,1-a]isoquinoline and 5.3 g. of benzoic acid in 50 ml of chlorobenzene at a bath temperature of 140° C. After refluxing the mixture for 1 hour, the solvent is removed by distillation. The residue is chromatographed over silica gel using chloroform as solvent. Compound A is obtained; m.p. = 132° C.

EXAMPLE 4

12 ml of a lithium butyl solution (20% in hexan) are added dropwise under nitrogen to 8 g. of (+)-N-(2-chloroacetyl-1,2,3,4-tetrahydroisoquinoline-1-methyl)-benzamid, dissolved in 300 ml dry tetrahydrofuran. The mixture is stirred for 2 hours and then refluxed for 12 hours. The solvent is removed by distillation after addition of water and the residue is dissolved in chloroform. The organic phase is washed with water, dried and the solvent is evaporated. Compound A is obtained; m.p. = 132° C.

The starting material can be obtained from (±)-1-cyano-2-benzoyl-1,2,3,4-tetrahydroisoquinoline which yields by hydrogenation in the presence of Raney-nickel at 100° C and a pressure of 100 atmospheres (±)-N-(1,2,3,4-tetrahydro-isoquinoline-1-methyl)-benzamide to which (+)-tartaric acid is added in methanolic solution. The tartaric acid salt of the (+)-isomer precipitates in the cold. The tartaric-acid-salt of the (−)-isomer is obtained from the mother-liquor and yields in the (+)-N-(1,2,3,4-tetrahydro-isoquinoline-1-methyl)-benzoic acid amide on alkalinisation; m.p. = 129° C, $[\alpha]_D^{20} = +27°$ C. The above-mentioned chloroacetyl compound, m.p. = 136° C, $[\alpha]_D^{20} = +87.2°$ C, may be obtained by reacting the (+)-N-(1,2,3,4-tetrahydro-isoquinoline-1-methyl)-benzoic acid amide with chloroacetic acid chloride in chloroform in the presence of triethylamine.

EXAMPLE 5

A slurry of 18.5 g. (+)-N-(2-chloroacetyl-1,2,3,4-tetrahydro-isoquinoline-1-methyl)-benzamide (m.p. = 136° C; $[\alpha]_D^{20} = +87.2°$ C; preparable by resolution of (±)-N-(1,2,3,4-tetrahydro-isoquinoline-1-methyl)-benzamide by (+)-tartaric acid and reaction of the (+)-isomer obtained with chloroacetic acid chloride in dichloromethan in the presence of sodium carbonate) in 200 ml of tert.-butanol is refluxed for 3 hours with a solution of potassium tert.-butylate prepared from 2.5 g of potassium and 100 ml of tert.-butanol. Compound A is obtained after decomposition by water and extraction with chloroform; m.p. = 132° C.

EXAMPLE 6 a. 1 g of (−)-N-(1,2,3,4-tetrahydro-isoquinoline-1-methyl-)-N-benzoyl-glycin (obtainable by reacting (−)-N-(1,2,3,4-tetrahydro-isoquinoline-1-methyl)-glycin dihydrochloride with benzoylchloride in chloroform in the presence of triethylamine) is heated to 180° C at a pressure of 15 mm Hg until the evolution of gas has ceased. The residue is dissolved in 50 ml of chloroform and the organic phase is washed subsequently with water, diluted aqueous hydrochloric acid, and with water again, then is dried and evaporated. Compound A is obtained; m.p. = 132° C.

b. 1.4 g benzoyl chloride, dissolved in 200 ml chloroform, are added at 20° C to 3.3 g of (−)-N-(1,2,3,4-tetrahydro-isoquinoline-1-methyl)-glycin dihydrochloride and 3.03 g of triethylamine both dissolved in 300 ml chloroform. The solvent is removed after 90 minutes and the residue is heated to 180° C for one hour. Then it is dissolved in chloroform, the solution is washed with water, diluted aqueous hydrochloric acid, aqueous sodium carbonate and water again, dried and evaporated. Compound A is obtained; m.p. = 132° C (crystallized from ethanol/ether).

EXAMPLE 7

30 g of crude (−)-N-(1,2,3,4-tetrahydro-isoquinoline-1-methyl)-N-benzoyl-glycin (obtainable following the method given in Example 6) are heated in 100 ml decahydronaphthalene for 2 hours at 180° C. After cooling the crystalline product formed is removed by filtration from the reaction mixture. Compound A is obtained; m.p. = 132° C (crystallized from ethanol/ether).

Pharmacological Examples compared with racemic 2-benzoyl-4-oxo-1,2,3,6,7,11b-hexahydro-pyrazino[2.1-a]isoquinoline (=compound B) and niclosamide).

EXAMPLE A

Hymenolepis nana, adults/mice

Hymenolepis microstoma, adults/mice

Test animals infected experimentally with H.nana or H.microstoma are treated 1-3 days after prepatent period of the parasites has elapsed. The effective agent is administered in the form of an aqueous suspension orally and subcutaneously respectively. The degree of effectiveness of the effective agent is determined by counting, after dissection, the worms remaining in the test animal as compared to untreated control animals and then calculating the percentage of effectiveness. The minimum effective dose is the minimum dose which achieves >90% reduction in worm count.

TABLE 1

| Effective Agent | Parasite | Minimum Effective Dose (mg/hg) |
|---|---|---|
| Compound A | H.nana adults | 20 |
|  | H.microstoma | 100 |
| Compound B | H.nana adults | 100 |
|  | H.microstoma | 250 |
| Niclosamide | H.nana adults | 500 |
|  | H.microstoma | <500 |

EXAMPLE B

Schistosoma mansoni/mice

Mice infected experimentally are treated immediately after the prepatent period of the parasites has elapsed. The effective compound is orally administered in the form of an aqueous suspension. The efficiency is determined by counting the living and the killed parasites after dissection of the test animals. The minimum effective dose is the minimum dose which achieves >95% kill.

TABLE 2

| Effective Compound | Minimum Effective Dose (mg/kg) |
|---|---|
| Compound A | 100 |
| Compound B | 200 |
| Lucanthone | 250 |

FORMULATION EXAMPLES

EXAMPLE I

Tablets to Combat Cestodes (Adults)

a. Tablets each containing 500 mg of Compound A as the effective agent are produced by processing a powder mixture consisting of 5 kg of Compound A, 3 kg of lactose, 1.8 kg of corn starch, and 0.2 kg of magnesium stearate.

b. The same mixture can be used to manufacture tablets containing 15 mg, 50 mg, 250 mg, and 1000 mg of Compound A.

The tablets containing 15 mg, 50 mg, and 250 mg of Compound A as the effective agent are preferably used for purposes of human medicine; all of the above-described tablets can be utilized for purposes of veterinary medicine.

EXAMPLE II

Tablets (Preferably) for Combating Cestode Cysticerci and/or Schistosomes

| (a) Effervescent Tablets Each tablet contains: | |
|---|---|
| Compound A | 400 mg |
| Citric acid | 320 mg |
| Sodium bicarbonate | 360 mg |
| Saccharin | 2 mg |
| Aromatic substance | as desired |
| Lubricant | as desired |
| Coloring agent | as desired |
| Sucrose | ad 1600 mg. |
| (b) Sweet Chewable Tablets Each tablet contains: | |
| Compound A | 800 mg |
| Cellulose | 32 mg |
| Sodium carboxymethylcellulose | 16 mg |
| Coloring agent and aromatic substance | as desired |
| Sucrose | ad 1600 mg |

EXAMPLE III

Dragees for Combating Cestodes in Human Medicine

| The dragee core contains: | |
|---|---|
| Compound A | 50 mg |
| Lactose | 30 mg |
| Corn starch | 18 mg |
| Magnesium stearate | 2 mg |

The dragee covering is composed of the following materials: talc, sucrose, titanium dioxide, calcium carbonate, polyvinyl-pyrrolidone, methylcellulose, glycerin, magnesium oxide, lacquer.

The same formulation can also be utilized for dragees containing 100 mg of A as the active substance.

EXAMPLE IV

Elixir to Combat Cestodes (Human Medicine)

| The elixir is produced by preparing a suspension from: | | |
|---|---|---|
| Compound A | 1.5 | kg. |
| Distilled water | 2 | l. |
| Buffer | 0.1 | l. |
| Glycerin | 3 | kg. |
| Sorbitol | 3 | kg. |
| Sucrose | 53 | kg. |
| Mixture of 60% methyl p-hydroxybenzoate and 40% propyl p-hydroxybenzoate | 0.1 | kg. |
| Ethanol | 12 | l. |

The mixture is mixed, if desired, with coloring agents and aromatic substances and filled up to 100 l. with distilled water.

EXAMPLE V

Capsules for Combating Cestodes and Schistosomes for Human and Veterinary Medicine

| Capsules of an appropriate size are filled with a mixture of: | |
|---|---|
| Compound A | 1000 mg |
| Talc | 50 mg |
| Magnesium stearate | 30 mg |

Capsules containing 200 mg. and 2,000 mg. of Compound A are produced correspondingly.

EXAMPLE VI

Injection Fluid for Purposes of Human and Veterinary Medicine

For subcutaneous administration in an oily or aqueous suspension, 15 ampoules are filled with a solution of 100 mg. of Compound A in 6 ml. of water and 4 ml. of propylene glycol with the addition of a solubilizer. The ampoules are either sterilized by heating or mixed with a preservative.

Ampoules containing 20 mg. of Compound A (for small animals) and 200 mg. of substance A (for large animals) are correspondingly produced.

EXAMPLE VII

Pellets

From the same parts by weight of Compound A and lactose, a powder mixture is produced which is processed together with sodium carboxymethylcellulose in the usual manner to a uniform granulated material having an average particle size of 1.5 mm.

EXAMPLE VIII

Premix for Purposes of Veterinary Medicine Suitable for Mixing with a Fodder as the Vehicle to Produce Medical Feed a. 25% Premix (Preferably for Larger Animals)
25 weight units of substance A is mixed with 75 weight units of fine bran (wheat middlings) and/or lactose.
b. 5% Premix (Preferably for Smaller Animals)
5 parts by weight of Compound A is processed analogously to Example VIII(a).

c. Use of a Premix Produced According to Example VIII(a) for Combating Moniezia Species in the Cattle Intestine In order to obtain a suitable medical fodder, 1 kg. of the premix produced according to Example VIII(a) is mixed with 9 kg. of a conventional concentrated feed. 80 g. of this medical fodder, containing 2,000 mg. of Compound A, is administered to each adult head of cattle to combat the Moniezia infestation.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:
1. A method of treating cestodial and trematodial infestations in animals which comprises administering to an animal infested with cestodes or trematodes an anthelmintically effective amount of (−) 2-benzoyl-4-oxo-1,2,3,6,7,11b-hexahydro-4H-pyrazino(2,1-a)-isoquinoline, substantially free from its (+) isomer.
2. A method according to claim 1, wherein the administration is oral.
3. A method according to claim 2, wherein the animal is infested with a cestode.
4. A method according to claim 1, wherein the animal is infested with a trematode of a species of Schistosoma.
5. A method according to claim 1 wherein the administration is parenteral.
6. A method according to claim 1 wherein the animal is a domestic animal.
7. A method according to claim 1 wherein the animal is a human being.
8. An anthelmintic composition adapted for oral ingestion comprising an anthelmintically effective unit dosage amount of (−) 2-benzoyl-4-oxo-1,2,3,6,7,11b-hexahydro-4H-pyrazino[2,1-a]isoquinoline, substantially free from its (+) isomer, in admixture with a comestible and in the form of a veterinary feed pre-mix or in admixture with a pharmaceutically acceptable carrier and in the form of a tablet, dragee, capsule or pellets.
9. A composition according to claim 8 in the form of a veterinary pre-mix.
10. A pharmaceutically acceptable composition according to claim 8 in the form of a tablet, dragee, capsule or pellets.

* * * * *